(12) United States Patent
Lauten et al.

(10) Patent No.: US 9,018,177 B2
(45) Date of Patent: Apr. 28, 2015

(54) COSMETIC COMPOSITIONS FOR INCREASING BIOAVAILABILITY OF THE ACTIVE COMPOUNDS BAICALIN AND/OR VITAMIN C

(71) Applicant: L'Oreal S.A., Paris (FR)

(72) Inventors: Elizabeth Hunter Lauten, New York, NY (US); Jean-Thierry Simonnet, Mamaroneck, NY (US); Zhi Pan, Fort Lee, NJ (US); Guive Balooch, New York, NY (US)

(73) Assignee: L'Oreal S.A., Paris (FR)

( * ) Notice: Subject to any disclaimer, the term of this patent is extended or adjusted under 35 U.S.C. 154(b) by 98 days.

(21) Appl. No.: 13/650,933

(22) Filed: Oct. 12, 2012

(65) Prior Publication Data
US 2014/0107047 A1    Apr. 17, 2014

(51) Int. Cl.
| | |
|---|---|
| A61K 9/00 | (2006.01) |
| A61K 47/12 | (2006.01) |
| A61K 47/22 | (2006.01) |
| A61K 31/7048 | (2006.01) |
| A61K 8/368 | (2006.01) |
| A61K 8/49 | (2006.01) |
| A61K 8/67 | (2006.01) |
| A61Q 19/00 | (2006.01) |

(52) U.S. Cl.
CPC .............. *A61K 9/0014* (2013.01); *A61K 47/12* (2013.01); *A61K 47/22* (2013.01); *A61K 31/7048* (2013.01); *A61K 8/368* (2013.01); *A61K 8/4913* (2013.01); *A61K 8/4953* (2013.01); *A61K 8/498* (2013.01); *A61K 8/675* (2013.01); *A61K 8/676* (2013.01); *A61Q 19/00* (2013.01); A61K 2800/10 (2013.01)

(58) Field of Classification Search
CPC ....... A61K 47/00; A61K 8/4973; A61K 8/60; A61K 31/7032; A61Q 19/00; A61Q 90/00
See application file for complete search history.

(56) References Cited

U.S. PATENT DOCUMENTS

| | | | |
|---|---|---|---|
| 3,501,409 A | | 3/1970 | Matson |
| 3,839,210 A | | 10/1974 | Beiswanger et al. |
| 4,680,143 A | | 7/1987 | Edge et al. |
| 5,532,012 A | | 7/1996 | Balentine et al. |
| 5,686,082 A | | 11/1997 | N'Guyen |
| 5,900,416 A | * | 5/1999 | Markson ...................... 424/728 |
| 6,121,209 A | | 9/2000 | Watts et al. |
| 6,331,520 B1 | | 12/2001 | Richardson |
| 6,355,657 B1 | | 3/2002 | Osborne |
| 6,423,327 B1 | | 7/2002 | Dobson, Jr. et al. |
| 6,479,442 B1 | | 11/2002 | Berube et al. |
| 6,645,513 B2 | | 11/2003 | Dobson, Jr. et al. |
| 6,646,035 B2 | | 11/2003 | Koch et al. |
| 6,733,797 B1 | | 5/2004 | Summers |
| 6,949,496 B1 | | 9/2005 | Boutique et al. |
| 7,452,549 B2 | | 11/2008 | Hasler-Nguyen et al. |
| 2002/0086042 A1 | | 7/2002 | Delrieu et al. |
| 2002/0110604 A1 | | 8/2002 | Babish et al. |
| 2003/0031715 A1 | | 2/2003 | Park et al. |
| 2003/0206972 A1 | | 11/2003 | Babish et al. |
| 2004/0146474 A1 | | 7/2004 | Galey |
| 2005/0158271 A1 | | 7/2005 | Lee et al. |
| 2005/0266121 A1 | | 12/2005 | Lines et al. |
| 2006/0110439 A1 | | 5/2006 | Tobia et al. |
| 2007/0208088 A1 | | 9/2007 | Lipshutz |
| 2007/0232561 A1 | | 10/2007 | Leung et al. |
| 2008/0095866 A1 | | 4/2008 | Declercq et al. |
| 2008/0176956 A1 | | 7/2008 | Hsu |
| 2008/0219927 A1 | | 9/2008 | Thakur et al. |
| 2009/0110674 A1 | | 4/2009 | Loizou |
| 2009/0233876 A1 | | 9/2009 | Auriol et al. |
| 2010/0047297 A1 | | 2/2010 | Petersen |
| 2011/0033525 A1 | | 2/2011 | Liu |
| 2011/0067294 A1 | | 3/2011 | Ng et al. |
| 2011/0136245 A1 | | 6/2011 | Parker |
| 2011/0152214 A1 | | 6/2011 | Boison et al. |
| 2012/0071550 A1 | | 3/2012 | Zelkha et al. |

FOREIGN PATENT DOCUMENTS

| | | | | |
|---|---|---|---|---|
| JP | 6150918 A | * | 3/1986 | ............. A61K 31/35 |
| WO | WO-2013016257 A1 | | 1/2013 | |

OTHER PUBLICATIONS

Mou, H., Wang, X., Lv, T., Xie, L., & Xie, H. (2011). On-line dissolution determination of Baicalin in solid dispersion based on near infrared spectroscopy and circulation dissolution system. Chemometrics and Intelligent Laboratory Systems, 105(1), 38-42.*
Makoto et al., JP 6150918 A, Mar. 1986, machine translation of abstract, http://worldwide.espacenet.com, and Derwent record from EAST. Retreived on Mar. 19, 2014.*
Suzuki, H. et al., "Mechanistic Studies on Hydrotropic Solubilization of Nifedipine in Nicotinamide Solution." *Chem. Pharm. Bull.* 46(1), 125-130 (1998).

(Continued)

*Primary Examiner* — Shaojia Anna Jiang
*Assistant Examiner* — Dale R Miller
(74) *Attorney, Agent, or Firm* — Novak Druce Connolly Bove + Quigg LLP

(57) ABSTRACT

Aqueous compositions comprising a) at least one active compound and b) at least one hydrotrope in an amount effective to increase transdermal penetration of the active compound, and methods for increasing bioavailability of active compounds are provided.

14 Claims, 3 Drawing Sheets

(56) References Cited

OTHER PUBLICATIONS

Evstigneev, M.P. et al., "Effect of a mixture of caffeine and nicotinamide on the solubility of vitamin (B2) in aqueous solution," *European Journal of Pharmaceutical Sciences* 28, 59-66 (2006).

Da Silva, R.C. et al., "Investigations on the mechanism of aqueous solubility increase caused by some hydrotropes." *Thermochimica Acta* 328, 161-167 (1999).

Huh, K.M. et al., "A new hydrotropic block copolymer micelle system for aqueous solubililzation of paclitaxel." *Journal of Controlled Release* 126, 122-129 (2008).

Takahashi, K. et al., "Application of hydrotropy to transdermal formulations: hydrotropic solubilization of polyol fatty acid monoesters in water and enchancement effect on skin permeation of 5-FU." *Journal of Pharmacy and Pharmacology* 63, 1008-1014 (2011).

Nicoli, S. et al., "Association of nicotinamide with parabens: Effect on solubility, partition and transdermal permeation." *European Journal of Pharmaceutics and Biopharmaceutics* 69, 613-621 (2008).

Nidhi, K. et al., "Hydrotropy: A Promising Tool for Solubility Enhancement: A Review." *International Journal of Drug Development & Research* 3(2), 26-33 (2011).

* cited by examiner

|  | Glucose Released from Lipids |
|---|---|
| control sample- lipids with no hydrotrope | 0% |
| 5% sodium salicylate | 82% |
| 3% sodium salicylate | 80% |
| 1% caffeine | 73% |
| 5% hydrovance | 73% |
| 3% niacinamide | 71% |
| 5% niacinamide | 68% |
| 3% hydrovance | 67% |
| 5% niacinamide +5% caffeine | 59% |
| 5% niacinamide +5% caffeine + 5% urea | 57% |
| 3% sodium PCA + 3% urea | 57% |
| 5% sodium PCA + 3% urea | 51% |
| 5% sodium PCA + 5% urea | 48% |
| 3% niacinamide + 5% caffeine | 46% |
| 5% sodium PCA | 19% |

COSMETIC COMPOSITIONS FOR INCREASING BIOAVAILABILITY OF THE ACTIVE COMPOUNDS BAICALIN AND/OR VITAMIN C

FIELD OF THE INVENTION

The present invention relates to aqueous compositions comprising at least one active molecule and at least one hydrotrope for increasing the bioavailability of the active molecule for topical applications.

BACKGROUND OF THE INVENTION

The cosmetic market has begun to include many active ingredients in formulations to help curb the effect of aging and skin damage. Unfortunately, the efficacy of some of these molecules is reduced due to the natural barrier properties of the skin membrane. In particular the outer most stratum corneum layer shows poor skin permeability of compounds that are hydrophilic, very lipophilic, of high molecular weight or charged.

For example, transdermal penetration of active molecules is especially relevant to products designed to protect skin from photoaging. In this case long UVA rays penetrate deep into the epidermis and produce free radicals which can cause long term health effects. Antioxidants are able protect the cells from this damage by scavenging free radicals and inhibiting oxidation reactions. However, research has shown that in order for many of active molecules, such as antioxidants to be effective they must also reside in the epidermis.

The most common technique to increase transdermal delivery is to use penetration enhancers. While many chemical penetration enhancers such as solvents work well to disrupt the lamellar lipid structure of the skin many of them are toxic, irritating, allergenic, or not suited to cosmetic formulations which cover large areas (unlike typical pharmaceutical transdermal patches).

Other techniques to increase transdermal delivery of active compounds rely on delivery systems such as liposomes in combination with solvents. U.S. 2006/0110439 discloses a delivery system containing liposomes and solvents to increase penetration of an active compound. U.S. Pat. No. 6,355,657 discloses a system for percutaneous delivery of the opioid loperamide that combines an organic solvent and fatty acid/fatty alcohol penetration enhancers, such as oleic acid, olleyl alcohol, ethoxydiglycol, laurocapram, alkanecarboxylic acid, dimethyl sulfoxide, polar lipids or n-methyl-2pyrrolidone.

While many cosmetic applications require the addition of penetration enhancers for efficacious actives, the enhancers must overcome the added challenges and needs of being safe, reversible and able to work in a cosmetic form or dose. In addition these enhancers must not interfere with the active molecule in such a way that compromises the molecule's activity. Thus, there is a need for compositions that increase the transdermal bioavailability of active compounds.

BRIEF SUMMARY OF THE INVENTION

The invention provides an aqueous composition comprising a) at least one active compound and b) at least one hydrotrope in an amount effective to increase transdermal penetration of the active compound. Preferably, the hydrotrope is a cosmetically acceptable hydrotrope, such as nicotinamide, caffeine, sodium PCA, or sodium salicylate. The active compound can be poorly water soluble, requiring the need to be solubilized by the hydrotrope itself (or a combination of hydrotropes), or a hydrophilic molecule that is readily dissolved.

Another aspect of the invention provides a method for increasing the bioavailability of an active molecule comprising applying an aqueous composition to skin, the composition comprising a) at least one active compound and b) at least one hydrotrope in an amount effective to increase transdermal penetration of the active compound.

A further aspect of the invention provides a method of preparing an aqueous composition comprising including in the composition at least one active compound and at least one hydrotrope in an amount effective to increase transdermal penetration of the active compound.

These and other aspects of the invention are shown in the appended claims, and described in greater detail in the detailed description of the invention.

DETAILED DESCRIPTION OF THE INVENTION

Figures 1, 2A:
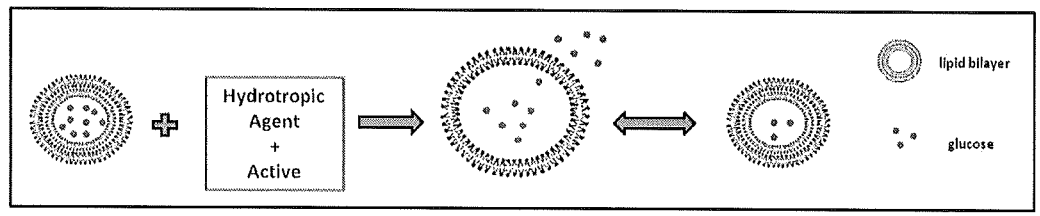
FIG. 1 shows a diagrammatic representation of the model lipid bilayer assay.
FIG. 2A and FIG. 2B show a table of glucose release from lipids in the presence of hydrotropes, and graph of glucose release after the presence of hydrotropes.

The present invention provides aqueous compositions comprising a) at least one active molecule and b) at least one hydrotrope in an amount effective to increase transdermal penetration of the active molecule.

Applicants have discovered that hydrotropes in cosmetic formulations enhance bioavailability of active molecules. The function of increased bioavailability is due to the ability of the hydrotrope to increase depth of penetration through the skin. Hydrotropes can be used in all cosmetic formulas which contain more than 5% water, for both topical application and injection.

Hydrotropes suitable for use in cosmetic compositions safely and reversibly disrupt the lamellar lipid crystalline layer of the stratum corneum in order to effectively deliver and increase bioavailability of active compounds in cosmetic formulations. When combined with poorly soluble and poorly penetrating active compounds such as polyphenols, adenosine, sugars, and hydrophilic molecules, hydrotropes increase penetration of the active compound through the skin.

As used herein, improving bioavailability of an active compound or molecule refers to increasing the amount of the active compound in skin, in comparison to a composition which does not contain the hydrotrope or hydrotropes present in the claimed aqueous compositions.

As used herein, increasing dermal penetration of an active compound or molecule refers to increasing the amount or depth of penetration, or both, of an active compound through skin, preferably human skin, in comparison with a composition which does not contain the hydrotrope or hydrotropes present in the claimed aqueous compositions, or does not contain such hydrotropes in amounts effective to increase transdermal penetration.

Hydrotropes (or hydrotropic agents) are a diverse class of water-soluble compounds that characterized by an amphiphilic molecular structure and ability to dramatically increase the solubility of poorly soluble organic molecules in water. Most hydrotropes have aromatic structure with an ionic moiety, while some of them are linear alkyl chains, as listed in the table below. Although hydrotropes noticeably resemble surfactants and have the ability to reduce surface tension, their small hydrophobic units and relatively shorter alkyl chain distinguish them as a separate class of amphiphiles. Consequently their hydrophobicity is not sufficient enough to create well organized self-associated structures, such as micelles, even with a high concentration.

Common hydrotropic molecules include: sodium 1,3-benzenedisulfonate, sodium benzoate, sodium 4-pyridinecarboxylate, sodium salicylate, sodium benzene sulfonate, caffeine, sodium p-toluene sulfonate, sodium butyl monoglycolsulfate, 4-aminobenzoic acid HCl, sodium cumene sulfonate, N,N-diethylnicotinamide, N-picolylnicotinamide, N-allylnicotinamide, 2-methacryloyloxyethyl phosphorylcholine, resorcinol, butylurea, pyrogallol, N-picolylacetamide 3.5, procaine HC1, proline HCl, nicotinamide, pyridine, 3-picolylamine, sodium ibuprofen, sodium xylenesulfonate, ethyl carbamate, pyridoxal hydrochloride, sodium benzoate, 2-pyrrolidone, ethylurea, N,N-dimethylacetamide, N-methylacetamide, and isoniazid. Hydrotropes can be found in Lee J. et al., "Hydrotropic Solubilization of Paclitaxel: Analysis of Chemical Structures for Hydrotropic Property", Pharmaceutical Research, Vol. 20, No. 7, 2003; and Hodgon T. K., Kaler E. W., "Hydrotropic Solutions", Current Opinion in Colloid and Interface Science, 12, 121-128, 2007.

Cosmetically acceptable hydrotropes refers hydrotropes that can be used in cosmetic compositions. While hydrotropes represent a broad class of molecules used in various fields, cosmetic applications will be limited due to safety and tolerance restrictions. Preferred hydrotropes in cosmetics are listed as below:

| Name of hydrotropes | Structure |
|---|---|
| Nicotinamide (Vit B3) | 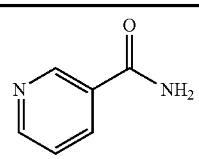 |
| Caffeine | 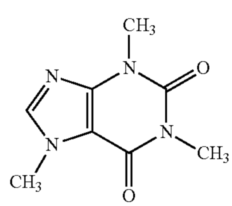 |
| Sodium PCA | 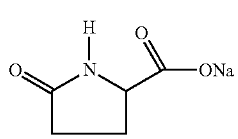 |
| Sodium Salicylate | 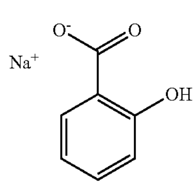 |

The suitability of a hydrotrope for use in cosmetic compositions can be determined using tests known in the art for determining effects of compounds on skin, and bioavailability methods.

At least one hydrotrope refers to one or a combination of two or more hydrotropes. One or combination of two or more hydrotropes can be used to improve the bioavailability of active compounds, or increase transdermal penetration of active compounds.

An advantage of using hydrotropes is, once a stable solution is obtained, further dilution doesn't influence the stability of the solution. This is very different from organic solvents that are commonly used to increase the water solubility of actives. Typically, an aqueous dilution of organic solvents with pre-dissolved actives results in crystallization or precipitation.

Hydrotropes which function to increase the penetration of active molecules in the skin can be selected using models of the skin, such as the model lipid bilayer assay disclosed herein the Examples. An effective hydrotrope solution allows the reversible disruption of lipids, taking into consideration the dose and potential combination of cosmetic hydrotropes.

The amount of hydrotrope present in the aqueous compositions will vary depending on the hydrotrope and the type and amount of active compound, preferably in the range of 0.01% to 20%, with respect to the total weight of the composition.

The inventive aqueous compositions comprise at least one active compound from various classes of compounds, such as compounds that are poorly water soluble (solubility<0.1%), such as polyphenols, and compounds that are hydrophilic, such as vitamin C.

The amount of active compound in the aqueous composition will depend on the identity of the active compound and its solubility in water, and the type and amount of hydrotrope present in the aqueous composition. Preferably, the amount ranges from 0.01% to 20%, based on the total weight of the composition.

Polyphenols are a structural class of natural, synthetic, and semisynthetic organic compounds that have multiple phenolic constituents. Polyphenols are normally available in plants and are very helpful to protect plants and also animals from usual health disorders and also the impacts of aging. Polyphenols function as potent free radical scavengers by donating their alcoholic hydrogen or one of their delocalized electrons. The two classes of polyphenols are flavonoids and non-flavonoids.

Flavonoids are a specific group of polyphenols, and are further categorized, according to chemical structure, into chalcones, flavones, flavanones, flavanols, flavonols, dihydroflavonols, isoflavonoids, neoflavonoids, catechins, anthocyanidins, and tannins. Over 4,000 flavonoids have been identified, many of which occur in fruits, vegetables and beverages (tea, coffee, beer, wine and fruit drinks). The flavonoids have been reported to have antiviral, anti-allergic, antiplatelet, anti-inflammatory, antitumor and antioxidant activities. Flavonoids protect lipids and vital cell components from damaging oxidative stress by efficiently scavenging free radicals.

Non-flavonoid polyphenols include lignans, aurones, stilbenoids, curcuminoids and other phenylpropanoids. Many of them are also well-known antioxidants like resveratrol, ferulic acid, curcumin, and pinoresinol.

At least one polyphenol is solubilized in the aqueous compositions, and the amount of polyphenol will depend on the specific polyphenol and the type and amount of hydrotrope present in the aqueous compositions. The amount of polyphenol present in the aqueous compositions can range from 0.01% to 20%; about 0.1% to about 10%; or about 0.1% to about 5%, based on the total weight of the composition.

Increasing the water solubility of polyphenols refers to increasing the solubility of the polyphenol in water in comparison with solubility of the polyphenol in water in the absence of the hydrotrope or hydrotropes.

If the active compound is poorly soluble in water, the at least one hydrotrope is present in the aqueous composition in amounts effective to increase the solubility of the active compound, such as a polyphenol, in water. The amount of hydrotrope will vary depending on the hydrotrope and the type and amount of the active compound. The amount of hydrotrope present in the aqueous compositions can range from 0.1% to 60%; about 0.1 to about 50%; or about 1% to 50%, based on the total weight of the composition.

The aqueous compositions can also comprise at least one additive conventionally used in the cosmetics field and which does not affect the properties of the compositions according to the invention, such as thickeners, fragrances, pearlescent agents, preservatives, sunscreens, anionic or nonionic or cationic or amphoteric polymers, proteins, protein hydrolysates, fatty acids, such as 18-methyleicosanoic acid, vitamins, panthenol, silicones, vegetable, animal, mineral or synthetic oils, gelling agents, antioxidants, solvents, fillers, screening agents, odor absorbers and coloring materials. These additives can be present in the composition according to the invention in proportions which are not limited, but which preferably fall in the range from 0 to 50% by weight, 5-40% by weight, or 30-50% by weight with respect to the total weight of the composition.

The aqueous compositions can comprise at least one active compound and at least one hydrotrope in an amount effective to increase transdermal penetration of the active compound, with water making up the remainder of the composition. Preferably, the composition comprises from 5% to 99.5% by weight of water, with respect to the total weight of the composition.

The pH of the aqueous compositions is not limited but is generally between 2 and 12 and preferably between 3 and 9. The pH can be adjusted to the desired value by addition of a base (organic or inorganic) to the composition, for example ammonia, sodium hydroxide, potassium hydroxide, or a primary, secondary or tertiary (poly)amine, such as monoethanolamine, diethanolamine, triethanolamine, isopropanolamine or 1,3-propanediamine, or with basic amino acids or poly amino acids like lysine, or arginine, or alternatively by addition of an inorganic or organic acid, preferably a carboxylic acid, such as, for example, citric acid.

Generally, any composition of the invention can be ingested, injected or topically applied to the skin (over any cutaneous region of the body) or to the mucous membranes (oral, jugal, gingival, genital, conjunctival, and the like).

Preferably, the compositions of the invention are topically applied onto the skin or mucous membranes. Depending on the method of administration under consideration, the composition can be provided in any dosage form normally used.

For topical application to the skin, the composition can have the form in particular of aqueous or oily solutions or of dispersions of the lotion or serum type, of emulsions with a liquid or semi-liquid consistency of the milk type, obtained by dispersion of a fatty phase in an aqueous phase (O/W) or vice versa (W/O), or of suspensions or emulsions with a soft consistency of the aqueous or anhydrous gel or cream type, or else of microcapsules or microparticles, or of vesicular dispersions of ionic and/or nonionic type or of foams. In fact any composition having between 5 to 99.5% of water phase is relevant. These compositions are prepared according to the usual methods.

For injection, the composition can be provided in the form of aqueous or oily lotions or in the form of serums. For the eyes, the composition can be provided in the form of drops and, for ingestion, it can be provided in the form of capsules, granules, syrups or tablets.

The amounts of the various constituents of the compositions according to the invention are those conventionally used in the fields under consideration.

In the cosmetics field, these compositions constitute in particular creams for cleaning, protecting, treating or caring for the face, for the hands, for the feet, for the major anatomical folds or for the body (for example, day creams, night creams, anti-aging creams, moisturizing creams, make-up-removing creams, foundation creams or sun creams), liquid foundations, make-up-removing milks, protective or care body milks, sun milks, lotions, gels or foams for caring for the skin, such as cleansing lotions, sun lotions, artificial tanning lotions, bath compositions, deodorizing compositions comprising a bactericidal agent, aftershave gels or lotions, depilatory creams, compositions for countering insect stings or bites, pain-relieving compositions or compositions for treating certain skin diseases, such as eczema, rosacea, psoriasis, lichen and severe pruritus.

Another aspect of the invention provides a method for preparing the aqueous compositions comprising including in the composition at least one active compound and at least one hydrotrope in an amount effective to increase transdermal penetration of the active compound. A hydrotrope solution is prepared by completely dissolving one or more hydrotropic agents into water, in an amount effective to increase transdermal penetration of the active compound. If the active compound is poorly soluble in water, the amount of hydrotrope should also be effective to solubilize the active compound. The active compound, such as a polyphenol, is then added in and mixed using stirring bar or any other mixer. A clear stable solution with a concentration that does not exceed the solubility of the active compound would be ready after more than one hour of mixing. No heat is necessary by following this procedure to dissolve polyphenols. Everything is prepared at room temperature to keep the stability of polyphenols. This is extremely useful to protect the activity of certain compounds and also makes the process much easier.

EXAMPLES

Example 1

Model Lipid Bilayer Assay

In this model system the lipid bilayers are able entrap a detectable compound and upon lipid disorder (i.e. in the presence of a hydrotrope) the compound can be released from the structure and measured in a chemical assay.

A representative lipid mixture (POLYGLYCERYL-3 CETYL ETHER (47.5%) (and) CHOLESTEROL (47.5% (and) DICETYL PHOSPHATE 5%) was selected for the lipid vesicles and glucose was chosen as the entrapped compound. Glucose release can be measured by glucose-oxidase assay using a Sigma HK assay kit. Higher glucose release in the presence of a hydrotrope suggests that that particular hydrotrope could have a greater effect in penetration improvement.

The experimental setup is as follows: 1% lipids were added to a 0.3M glucose solution and stirred for 6 hours (rpm 1100) at 85° C. Final lipid solution was dialysized for 24 hrs in 0.7% NaCl bath using a 3.5 Kd dialysis membrane in order to remove any free glucose in the supernatant. To ensure the remaining glucose is fully entrapped in the lipid vesicle the supernatant is measured by the glucose oxidase kit. As a control the lipid vesicles can be broken by n-octylglucoside and the entrapped glucose can be measured.

Figure 2B:
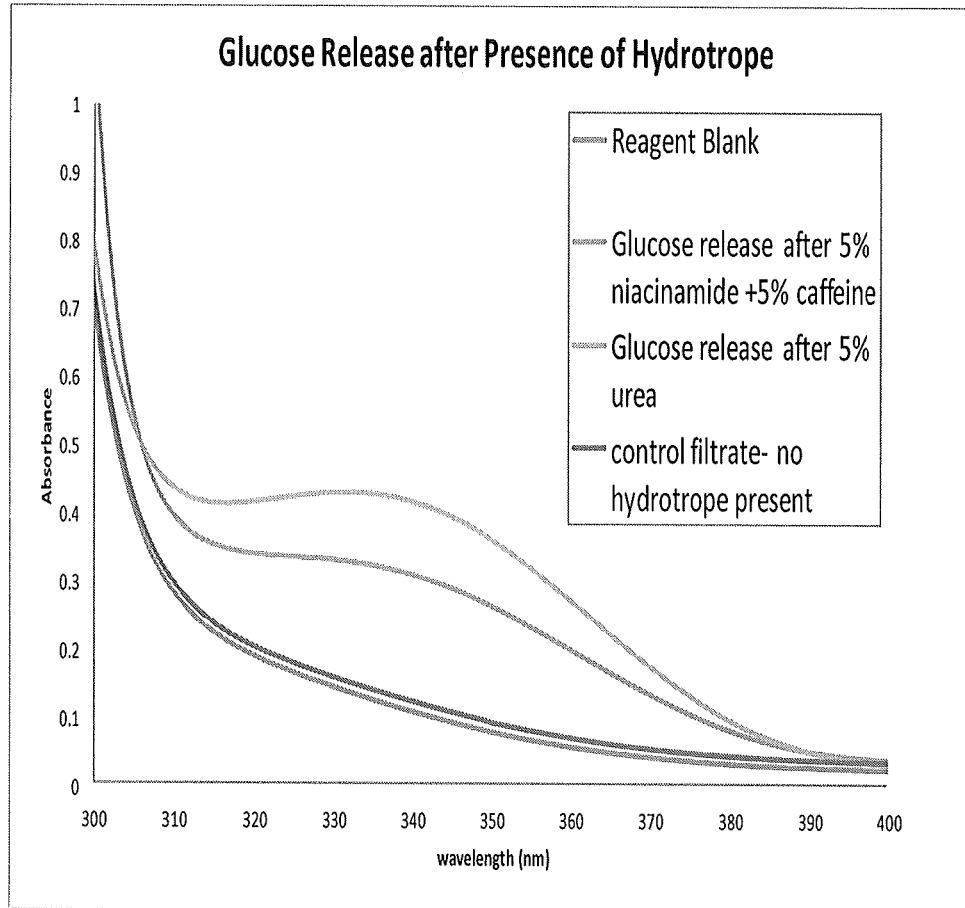

The results shown in FIG. 2 represent a lipid suspension that was incubated with hydrotropes for 20 hours. The higher release of glucose suggests a more efficient hydrotrope or combination of hydrotropes. The following hydrotropes were tested both for dose response and potential synergy when combined with each other: caffeine, niacinamide, NaPCA, and sodium salicylate.

Hydrotropes or combinations of hydrotropes with >15% glucose release were selected as preferred hydrotropes for formulations.

Example 2

Ex-Vivo Testing of Hydrotropes as Penetration Enhancers

To further evaluate the effect of penetration enhancers on human skin we performed CARS (coherent anti-stokes raman spectroscopy) experiments. Using this technique we are able to follow the penetration depth of antioxidants in human ex-vivo skin and compare the variability between a formulation containing no hydtotropes, one hydrotrope, and combination of hydrotropes.

Figures 3A, 3B:
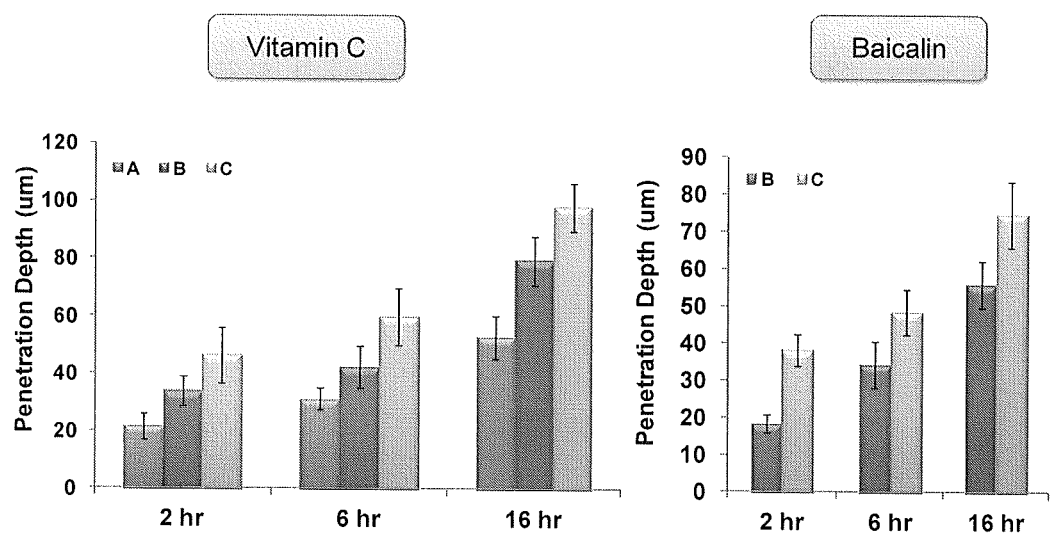
FIG. 3A and FIG. 3B show graphs of the depth of penetration of vitamin C and baicalin in human ex-vivo skin.

The results in FIG. 3 show the penetration depth of the antioxidants vitamin C and baicalin (solubilised by niacinamide and caffeine) in ex-vivo human skin after 2, 6, and 16 hours with the following formulas—Formula A (glycol serum with 10% vitamin C), Formula B (glycol serum with 10% vitamin C, 0.5% baicalin, and 5% caffeine), and Formula C (glycol serum with 10% vitamin C, 0.5% baicalin, 5% caffeine and 5% niacinamide). Formula A does not contain baicalin as it requires the addition of some hydrotropes for aqueous solubility. In FIG. 3A, Formula A is represented by the left column; Formula B by the middle column; and Formula C by the right column. In FIG. 3B, Formula B is represented by the left column; and Formula C by the right column.

The results clearly show that the addition of hydrotropes to formulations increases the penetration depth of the antioxidant molecules. In this case the synergy of niacinamide and caffeine allow for the highest penetration depth of both vitamin C and baicalin.

Of interesting note, baicalin requires the association of hydrotropes in order to achieve efficient levels in aqueous environments while vitamin C is highly hydrophilic and does not. However, the addition of hydrotropes in the final formulation improves the penetration depth of both molecules.

Example 3

Compatible Formula Compositions 3.1 Serum
The serum was prepared using the following method:

| PHASE | INCI US Name | CONCENTRATION (wt %) |
| --- | --- | --- |
| A | DIPROPYLENE GLYCOL | 10 |
| A | PEG-4 | 10 |
| A | BAICALIN | 0.4 |
| B | ALCOHOL DENATURED | 10 |
| C | WATER | 49.5 |
| C | ASCORBIC ACID | 10 |
| C | CAFFEINE | 5 |
| C | NIACINAMIDE | 5 |

-continued

| PHASE | INCI US Name | CONCENTRATION (wt %) |
| --- | --- | --- |
| C | BAICALIN | 0.1 |
| PH | SODIUM HYDROXIDE | 0 |

The compounds of phase A were combined and heated to ~65-75° C. under constant stirring. Phase A was then cooled and phase B was added. Separately, the compounds of phase C were combined and mixed under constant stirring at room temperature. Phase A+B was added to phase C and stirred for one hour to form the serum. The pH of the serum was adjusted to 4.5 with sodium hydroxide.

3.2 Oil in Water Emulsion
The oil in water emulsion was prepared using the following method:

| PHASE | INCI US Name | Concentration (wt %) |
| --- | --- | --- |
| A | WATER | 46.78 |
| A | NIACINAMIDE | 2.7 |
| A | CAFFEINE | 2.7 |
| A | BAICALIN | 0.27 |
| A | POLYSORBATE 61 | 0.36 |
| A | PHENOXYETHANOL | 0.5 |
| A | SODIUM STEAROYL GLUTAMATE | 0.4 |
| A | DISODIUM EDTA | 0.1 |
| B | OCTOCRYLENE | 2.5 |
| B | ISOPROPYL LAUROYL SARCOSINATE | 5 |
| B | OCTYLDODECANOL (and) OCTYLDODECYL XYLOSIDE | 0.86 |
| B | GLYCERYL STEARATE | 0.29 |
| B | STEARYL ALCOHOL | 0.14 |
| B | CAPRYLYL GLYCOL | 0.3 |
| B | p-ANISIC ACID | 0.1 |
| B | ISOTRIDECYL ISONONANOATE | 32 |
| B | BASF W RP | 5 |

The compounds of phase A were combined and heated to 80-85° C. mixing slowly (500-700 rpm) until all dissolved. Separately, the compounds of phase B were combined and heated to ~80-85° C. mixing slowly (500-700 rpm) until all dissolved. Phase B was added to phase under mixing conditions (Rayneri). The mixing speed was increased and the mixture was emulsified for thirty minutes. Particle size was then checked under a microscope. The resultant oil in water emulsion was cooled to 25° C. with slower speed mixing. The emulsion was then run under a high pressure homogenizer.

What is claimed is:
1. An aqueous cosmetic skin-care composition comprising;
(a) about 0.5 wt. % of baicalin and/or about 10 wt. % vitamin C;
(b) about 5 wt. % of each of the hydrotropes caffeine and niacinamide, wherein the amount of said hydrotropes is effective to increase transdermal penetration of baicalin and/or vitamin C; and
(c) water;
wherein said skin care composition is in the form of a lotion, serum, gel, milk, foam, liquid foundation, or cream, and is suitable for topical application to the skin.
2. The composition of claim 1, wherein the composition is a serum.
3. The composition of claim 2, wherein the serum further comprises dipropylene glycol, PEG-4, and/or alcohol.
4. The composition of claim 1, wherein the composition is an oil-in-water emulsion.

5. The composition of claim 4, wherein the oil-in-water emulsion further comprises: polysorbate 61, phenoxyethanol, sodium stearoyl glutamate, disodium EDTA, octocrylene, isopropyl lauroyl sarcosinate, octyldodecanol (and) oxyldodecyl xyloside, glyceryl stearate, stearyl alcohol, caprylyl glycol, p-anisic acid, and/or isotridecyl isononanoate.

6. The composition of claim 1, further comprising:
(d) at least one additive conventionally used in the cosmetics field selected from the group consisting of a thickener, a fragrance, a pearlescent agent, a preservative, a sunscreen, an anionic polymer, a nonionic polymer, a cationic polymer, an amphoteric polymer, a protein, a protein hydrolysate, a fatty acid, a vitamin, panthenol, a silicone, a vegetable oil, an animal oil, a mineral oil, a synthetic oil, a gelling agent, an antioxidant, a solvent, a filler, an odor absorber, and a coloring material.

7. A method for increasing the bioavailability of vitamin C and/or baicalin comprising topically applying to skin an aqueous cosmetic skin-care composition according to claim 1.

8. A method for protecting skin from photoaging comprising applying a composition according to claim 1 to the skin.

9. An aqueous cosmetic skin-care composition comprising; (a) about 0.5 wt. % of baicalin and about 10 wt. % vitamin C;
(b) about 5 wt. % of each of the hydrotropes caffeine and niacinamide, wherein the amount of said hydrotropes is effective to increase transdermal penetration of baicalin and vitamin C;
(c) water; and
(d) at least one additive conventionally used in the cosmetics field selected from the group consisting of a thickener, a fragrance, a pearlescent agent, a preservative, a sunscreen, an anionic polymer, a nonionic polymer, a cationic polymer, an amphoteric polymer, a protein, a protein hydrolysate, a fatty acid, a vitamin, panthenol, a silicone, a vegetable oil, an animal oil, a mineral oil, a synthetic oil, a gelling agent, an antioxidant, a solvent, a filler, an odor absorber, and a coloring material;
wherein said skin care composition is in the form of a lotion, serum, gel, milk, foam, liquid foundation or cream and is suitable for topical application to the skin.

10. The composition of claim 9, wherein the composition is a serum.

11. The composition of claim 9, wherein the composition further comprises dipropylene glycol, PEG-4, and/or alcohol.

12. The composition of claim 9 comprising 5 wt. % to 40 wt. % of component (d).

13. A method for increasing the bioavailability of vitamin C and/or baicalin comprising topically applying to skin an aqueous cosmetic skin-care composition according to claim 9.

14. A method for protecting skin from photoaging comprising applying a composition according to claim 9 to the skin.

* * * * *